(12) United States Patent
Borden et al.

(10) Patent No.: US 6,906,801 B2
(45) Date of Patent: *Jun. 14, 2005

(54) MEASURING A PROPERTY OF A LAYER IN MULTILAYERED STRUCTURE

(75) Inventors: Peter G. Borden, San Mateo, CA (US); Jiping Li, Fremont, CA (US)

(73) Assignee: Applied Materials, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/722,724

(22) Filed: Nov. 25, 2003

(65) Prior Publication Data

US 2004/0119978 A1 Jun. 24, 2004

Related U.S. Application Data

(63) Continuation of application No. 10/269,619, filed on Oct. 11, 2002, now abandoned, which is a continuation of application No. 09/544,280, filed on Apr. 6, 2000, now Pat. No. 6,489,801, which is a continuation of application No. 09/095,804, filed on Jun. 10, 1998, now Pat. No. 6,049,220.

(51) Int. Cl.$^7$ .............................................. G01N 21/55
(52) U.S. Cl. ..................................................... 356/432
(58) Field of Search ................................. 356/432, 445

(56) References Cited

U.S. PATENT DOCUMENTS

| 3,462,602 A | 8/1969 | Apple ........................... 250/83 |
| 3,909,602 A | 9/1975 | Micka ........................... 235/151 |
| 3,930,730 A | 1/1976 | Laurens et al. .............. 356/106 |

(Continued)

FOREIGN PATENT DOCUMENTS

| EP | 0 718 595 | 12/1995 | ........... G01B/11/06 |
| JP | 05006929 A | 1/1993 | ........... H01L/21/66 |
| JP | 2000009443 A | 1/2000 | |
| WO | 97/08536 | 6/1997 | ........... G01N/21/00 |
| WO | 99/64880 | 12/1999 | ........... G01R/31/26 |

OTHER PUBLICATIONS

Intl Prel Search Report PCT/US03/29993.
Jackson, "Classical Electrodynamics", John Wiley & Sons, Inc., (month unavailable), 1967, pp. 222–226.
Rosencwaig et al. "Detection of Thermal Waves Through Optical Reflectance", Appl Phys. Lett. 46, Jun. 1985, pp1013–1015.

(Continued)

*Primary Examiner*—Richard A. Rosenberger
(74) *Attorney, Agent, or Firm*—Silicon Valley Patent Group LLP

(57) ABSTRACT

An apparatus measures a property of a layer (such as the sheet resistance of a conductive layer or thermal conductivity of a dielectric layer that is located underneath the conductive layer) by performing the following method: (1) focusing the heating beam on the heated a region (also called "heated region") of the conductive layer (2) modulating the power of the heating beam at a predetermined frequency that is selected to be sufficiently low to ensure that at least a majority (preferably all) of the generated heat transfers out of the heated region by diffusion, and (3) measuring the power of another beam that is (a) reflected by the heated region, and (b) modulated in phase with modulation of the heating beam. The measurement in act (3) can be used directly as a measure of the resistance (per unit length) of a conductive line formed by patterning the conductive layer. Acts (1)–(3) can be repeated during fabrication of a semiconductor wafer, at each of a number of regions on a conductive line, and any change in measurement indicates a corresponding change in resistance of the line. When the measurement changes by more than a predetermined amount (e.g. by 10%), a process parameter that controls the fabrication process is changed to return the measurement to normal in the next wafer. Moreover, the thermal conductivity of the dielectric layer can be measured, or monitored for changes beyond a predetermined limit during a scan across the wafer, if resistance is known.

17 Claims, 6 Drawing Sheets

U.S. PATENT DOCUMENTS

| | | | |
|---|---|---|---|
| 4,243,327 A | 1/1981 | Frosch et al. | 356/432 |
| 4,255,971 A | 3/1981 | Rosencwaig | 73/606 |
| 4,455,741 A | 6/1984 | Kolodner | 29/574 |
| 4,466,748 A | 8/1984 | Needham | 374/129 |
| 4,468,136 A | 8/1984 | Murphy et al. | 374/45 |
| 4,521,118 A | 6/1985 | Rosencwaig | 374/5 |
| 4,522,510 A | 6/1985 | Rosencwaig et al. | 374/7 |
| 4,571,685 A | 2/1986 | Kamoshida | 364/468 |
| 4,579,463 A | 4/1986 | Rosencwaig et al. | 374/57 |
| 4,632,561 A | 12/1986 | Rosencwaig et al. | 356/432 |
| 4,634,290 A | 1/1987 | Rosencwaig et al. | 374/5 |
| 4,636,088 A | 1/1987 | Rosencwaig et al. | 374/5 |
| 4,679,946 A * | 7/1987 | Rosencwaig et al. | 356/445 |
| 4,710,030 A | 12/1987 | Tauc et al. | 356/445 |
| 4,750,822 A | 6/1988 | Rosencwaig et al. | 324/445 |
| 4,795,260 A | 1/1989 | Schuur et al. | 356/400 |
| 4,854,710 A | 8/1989 | Opsal et al. | 356/432 |
| 4,950,990 A | 8/1990 | Moulder et al. | 324/224 |
| 4,952,063 A | 8/1990 | Opsal et al. | 356/432 |
| 4,975,141 A | 12/1990 | Greco et al. | 156/626 |
| 4,996,659 A | 2/1991 | Yamaguchi et al. | 714/736 |
| 5,042,951 A | 8/1991 | Gold et al. | 356/369 |
| 5,042,952 A | 8/1991 | Opsal et al. | 356/432 |
| 5,074,669 A | 12/1991 | Opsal | 356/447 |
| 5,149,978 A | 9/1992 | Opsal et al. | 250/234 |
| 5,159,412 A | 10/1992 | Willenborg et al. | 356/445 |
| 5,181,080 A | 1/1993 | Fanton et al. | 356/381 |
| 5,228,776 A | 7/1993 | Smith et al. | |
| 5,408,327 A | 4/1995 | Geiler et al. | 356/432 |
| 5,430,548 A | 7/1995 | Hiroi et al. | 356/394 |
| 5,454,004 A | 9/1995 | Leger | 372/99 |
| 5,574,562 A | 11/1996 | Fishman et al. | 356/432 |
| 5,652,716 A | 7/1997 | Battersby | 703/13 |
| 5,657,754 A | 8/1997 | Rosencwaig | 128/633 |
| 5,667,300 A | 9/1997 | Mandelis et al. | 374/43 |
| 5,706,094 A * | 1/1998 | Maris | 356/432 |
| 5,741,614 A | 4/1998 | McCoy et al. | 430/30 |
| 5,761,082 A | 6/1998 | Miura-Mattausch | 703/14 |
| 5,764,363 A | 6/1998 | Ooki et al. | 356/364 |
| 5,790,251 A | 8/1998 | Hagiwara | 356/351 |
| 5,877,860 A | 3/1999 | Borden | 356/376 |
| 5,883,518 A | 3/1999 | Borden | 324/752 |
| 5,966,019 A | 10/1999 | Borden | 324/752 |
| 5,978,074 A | 11/1999 | Opsal et al. | 356/72 |
| 6,049,220 A | 4/2000 | Borden et al. | 324/765 |
| 6,054,868 A | 4/2000 | Borden et al. | 324/752 |
| 6,081,334 A | 6/2000 | Grimbergen et al. | 356/357 |
| 6,154,280 A | 11/2000 | Borden | 356/376 |
| 6,169,601 B1 | 1/2001 | Eremin et al. | 356/240 |
| 6,211,961 B1 | 4/2001 | Maris | 356/432 |
| 6,268,916 B1 | 7/2001 | Lee et al. | 356/432 |
| 6,281,027 B1 | 8/2001 | Wei et al. | 438/14 |
| 6,323,951 B1 | 11/2001 | Borden et al. | 356/502 |
| 6,327,035 B1 | 12/2001 | Li et al. | 356/432 |
| 6,336,969 B1 | 1/2002 | Yamaguchi et al. | 117/7 |
| 6,395,563 B1 | 5/2002 | Eriguchi | 438/7 |
| 6,400,454 B1 | 6/2002 | Noguchi et al. | 356/237 |
| 6,426,644 B1 | 7/2002 | Borden et al. | 324/765 |
| 6,483,594 B2 | 11/2002 | Borden et al. | 356/502 |
| 6,486,965 B1 | 11/2002 | Kim | 356/626 |
| 6,489,624 B1 | 12/2002 | Ushio et al. | 250/559 |
| 6,489,801 B1 | 12/2002 | Borden et al. | 324/766 |
| 6,528,333 B1 | 3/2003 | Jun et al. | 438/16 |
| 6,559,942 B2 | 5/2003 | Sui et al. | 356/369 |
| 6,694,284 B1 | 2/2004 | Nikoonahad et al. | 702/155 |
| 6,734,968 B1 | 5/2004 | Wang et al. | 356/369 |
| 2002/0126732 A1 | 9/2002 | Shakouri et al. | 374/130 |
| 2003/0155927 A1 | 8/2003 | Pinto et al. | 324/501 |

OTHER PUBLICATIONS

Rosencwaig, "Thermal–Wave Imaging", Science, vol. 218, No. 4569, Oct. 1982, pp. 223–228.

Opsal et al. "Thermal–Wave Detection and Thin–Film Thickness Measurements with Laser Beam Deflection", Applied Optics, vol. 22, No. 20, Oct. 1983, pp. 3169–3176.

"Process Monitoring System," Quantox Product Brochure, 3 pg, prior to Nov. 2003.

J. Kolzer et al "Thermal Imaging and Measurement Techniques for Electronic Materials and Devices" Microelectronic Engineering, vol. 31, 1996 (month unknown) pp. 251–270.

C. Martinsons et al. "Recent progress in the measurment of thermal properties of hard coatings" Thin Solid Films, vol. 317, Apr. 1998, 455–457.

S. Wolf and R. N. Tauber, "Silicon Processing For The VLSI Era", vol. 1, 1986, pp. 388–399.

Yaozhi Hu and Sing Pin Tay, "Spectroscopic ellipsometry investigation of nickel silicide formation by rapid thermal process", J. Vac. Sci. Technology, American Vacuum Soc. May/Jun. 1998, pp. 1820–1824.

Quality Today News, article entitled "In–Line Metrology SEM System with 3D Imaging" dated Jan. 10, 2000 and published at http://www.qualitytoday.com/Jan–00–news/011000–3.htm before Apr. 4, 2001.

Walter G. Driscoll and William Vaughan, "Handbook of Optics", 1978, pp. 8–42, 8–43, 8–107, and 10–72 to 10–77.

Charles Kittel, "Introduction to Solid State Physics", Fourth Edition, John Wiley & Sons, published prior to Mar. 1, 2002, pp. 262–264.

Rolf E. Hummel, "Electronic Properties of Materials, An Introduction For Engineers", published prior to Mar. 1, 2002, pp. 137–145.

H.S. Carslaw and J.C. Jaeger, "Conduction of Heat In Solids", Second Edition, published prior to Mar. 1, 2002, pp. 64–66.

A. Rosencwaig, "Thermal Wave Measurement of Thin–Film Thickness", 1986 American Chemical Society, pp. 182–191.

A. Rosencwaig et al., "Thin–Film Thickness Measurements with Thermal Waves", Journal de Physique, Oct. 1983, pp. C6–483 – C6–489.

W. L. Smith et al. "Thermal–wave Measurements and Monitoring of TaSIx Silicide Film Properties" J. Vac. Technol.B2(4), Oct.–Dec. 1984, pp. 710–713.

A. Salnick et al., "Nonlinear Fundamental Photothermal Response in 3D Geometry: Experimental Results for Tungsten", (believed to be prior to Mar. 1, 2002).

S. Ameri et al., "Photo–Displament Imaging", Mar. 30, 1981, pp. 337–338.

L. Chen et al., "Thermal Wave Studies of Thin Metal Films Using the Meta–Probe–A New Generation Photothermal System" 25th Review of Progress in QNDE, Snowbird, UT Jul. 19–24, 1998, pp 1–12.

P. Alpern and S. Wurm, "Modulated Optical Reflectance Measurements on Bulk Metals and Thin Metallic Layers", J. Appl. Phys. 66(4), Aug. 15, 1989, pp 1676–1679.

J. Opsal, "The Application of Thermal Wave Technology to Thickness and Grain Size Monitoring of Aluminum Films", SPIE vol. 1596 Metalization Performance and Reliability Issues for VLSI and ULSI (1991), pp 120–131.

A. Rosenwaig, "Process Control In IC Manufacturing With Thermal Waves", Review of Progress in Quantitative Nondestructive Evaluation, vol. 9, 1990, pp 2031–2037.

K. Farnaam, "Measurement of Aluminum Alloy Grain Size on Product Wafers and its Correlation to Device Reliability", 1990 WLR Final Report, pp 97–106.

B.C. Forget et al., "High Resolution AC Temperature Field Imaging", Electronic Letters Sep. 25, 1997, vol. 33 No. 20, pp 1688–1689.

C. Paddock et al., "Transient Thermoreflectance from Metal Films", May 1986 vol. 11, No. 5 Optical Letters, pp 273–275.

C. Paddock et al., "Transient Thermoreflectance from Metal Films", J. Appl. Phys. 60(1), Jul. 1, 1986, pp 285–290.

Per–Eric Nordail et al. "Photothermal Radiometry", Physica Scripts, vol. 20, 659–662, 1979.

A. Rosenwaig, "Thermal Wave Monitoring and Imaging of Electronic Materials and Devices", pp 73–109.

A. Rosenwaig, "Applications of Thermal–Wave Physics to Microelectronics", VLSI Electronics, Microstructure Science vol. 9, 1995, pp 227–288.

W. Lee Smith et al., "Voids, Notches and Micros=cracks in Al Metallization Detected by Nondestrictive Thermal Wave Imaging", Jun. 23m 1989, pp. 211–221.

W. Lee Smith et al., Imaging of Subsurface Defects in ULSI Metalization (Al Voids SI Preciptates, Silicide Instability) and SI Substrates (D Defects), Technical Proceedings Simicon/Japan 1992, Nippon Convention Center, Japan pp 238–246.

W. Lee Smith, "Nondestructive Thermal Wave Imaging of Voids & Microcracks in Aluminum Metallization", 1989 WLR Final Report, pp 55–68.

W. Lee Smith, "Direct Measurement of Stress–Induced Void Growth by Thermal Wave Modulated Optical Refectance Imaging", 1991 IEEE/IRPS, pp 200–208.

W. Lee Smith, "Evaluating Voids and Microcracks in Al Metalization", Semiconductor International, Jan. 1990, pp 232–237.

C. G. Welles et al., "High–Resolution Thermal Wave Imaging of Surface and Subsurface Defects in IC Metal Lines", Materials Research Society, SF Marriott, Apr. 27–May 1, 1992, pp 1187–1191.

L. Fabbri et al., "Analysis of Local Heat Transfer Properties of Tape–cast AIN Ceramics Using Photothermal Reflectance Microscopy", 1996 Chapman & Hall, pp 5429–5436.

J. A. Batista et al., "Biased MOS–FET and Polycrystalline Silicon Tracks Investigated by Photothermal Refelctance Microscopy", pp 468–469.

L. Chen et al., "Meta–Probe: A New Generation Photothermal System For Thin Metal Films Characterization" (believed to be prior to Mar. 1, 2002).

L. Chen et al., "Thermal Wave Studies of Thin Metal Films and Structures", (believed to be prior to Mar. 1, 2002).

9th Interantaional Conference on Photoacoustic and Photothermal Phenomena Conference Digest, Jun. 27–30, 1996 Nanjing, P.R. China, pp 81.

R. S. Sharpe, Research Techniques in Nondestructive Testing vol. VII, Academic Press 1984, pp 158–365.

R. L. Thomas et al., " Thermal Wave Imaging For Nondestructive Evaluation" 1982 Ultrasonic Symposium, pp 586–590.

G. Slade Cargill III, "Electron–Acoustic Microscopy", Physics Today, Oct. 1981, pp 27–32.

A. Rosencwaig, "Thermal Wave Microscopy", Solid State Technology, Mar. 1982, pp 91–97.

Eric A. Ash, "Acoustical Imaging" vol. 12, Plenium Press, Jul. 19–22, 1982, pp 61–65.

Paquin, "Properties of Metals", Handbook of Optics, vol. II, McGraw–Hill, Inc. (month unavailable), 1995, pp. 35.3–35.7.

Schroder, "Semiconductor Material and Device Characterization", John Wiley & Sons, Inc. (month unavailable), 1990, pp2–20, 84–85, 232–235, 304–306, 364, 367–374, 378–383.

J. Opsal, "High Resolution Thermal Wave Measurements and Imaging of Defects and Damage in Electronic Materials" Photoacoustic and Photothermal Phenomena II, Springer Series in Optical Sciences, vol. 62, Springer Verlag Berlin, Heidelberg, 1990.

Rosencwaig, "Thermal Wave Characterization and Inspection of Semiconductor Materials and Devices", Chapter 5 (pp. 97–135) of Photoacoustic and Thermal Wave Phenomena in Semiconductors, North Holland (month unavailable) 1987.

Constantinos Christofides "Photomodulated Thermoreflectance Investigation of Semiconducting Implanted Wafers," Microelectronic Engineering, 40 (1998), 251–261.

Bristow, Thomas C. and Dag Lindquist, "Surface Measurements With A Non–Contact Nomarski–Profiling Instrument", Interferometric Metrology, SPIE vol. 816, Aug. 1987, pp. 106–110.

"Process Monitoring System", Quantox Product Brochure, 3 pages, published prior to Mar. 1, 2002.

International Search Report PCT/US99/12999.

International Search Report PCT/US03/06239.

International Search Report PCT/US01/07475.

International Search Report PCT/US03/06379.

International Search Report PCT/US03/02650.

* cited by examiner

MEASURING A PROPERTY OF A LAYER IN MULTILAYERED STRUCTURE

CROSS-REFERENCE TO RELATED APPLICATIONS

This application is a continuation application of U.S. patent application Ser. No. 10/269,619 filed Oct. 11, 2002 now abandoned by Peter G. Borden, Regina G. Nijmeijer and Jiping Li, which is in turn a continuation of Ser. No. 09/544,280 filed Apr. 6, 2000 now issued as U.S. Pat. No. 6,489,801 which is itself a continuation of Ser. No. 09/095,804 filed Jun. 10, 1998 now issued as U.S. Pat. No. 6,049,220.

This application presents the same material as presented in U.S. patent application Ser. No. 09/095,805 now U.S. Pat. No. 6,054,868, which was previously incorporated by reference in each of the applications identified in the previous paragraph.

This application is also related to and incorporates by reference in their entirety each of the following commonly owned U.S. patent applications:

Ser. No. 08/638,944, filed Apr. 24, 1996, now U.S. Pat. No. 5,883,518;

Ser. No. 08/637,244, filed Apr. 24, 1996, now U.S. Pat. No 5,966,019;

Ser. No. 09/095,805 filed Jun. 10, 1998, now U.S. Pat. No. 6,054,868; and

Ser. No. 09/095,804 filed Jun. 10, 1998, now U.S. Pat. No. 6,049,220.

BACKGROUND OF THE INVENTION

Description of Related Art

Metal lines having sub-micron (i.e. less than 1 micron) dimensions are conventionally used to interconnect devices that are formed in an integrated circuit die. Such a metal line is typically formed as a portion of a film of metal (such as aluminum or copper). The metal film is normally formed as a blanket layer over a semiconductor wafer, and is thereafter removed (e.g. by etching) to form one or more metal lines, in a process act known as "patterning". Conventionally, the resistivity of the metal film is measured (on a test wafer), and the measurement is combined with a measurement of the film's thickness (on another test wafer) and, a measurement of the line width (on a production wafer), to determine if the metal film has ohmic loss sufficiently low for use in forming metal lines required in an integrated circuit die.

A number of methods exist for measuring a metal film's resistivity. Two such methods are commonly known as "probing" and "eddy current". In the probing method, two or four probes are brought into physical contact with an unpatterned metal film (e.g. on a test wafer) to measure the film's resistivity directly. See, for example, "The Four-Point Probe", Section 1.2, pages 2–20 in the book "Semiconductor Material and Device Characterization" by Dieter K. Schroder, John Wiley & Sons, Inc, New York, 1990. In the eddy current method, a measurement device is coupled to the metal film either capacitively or inductively, i.e. without contacting the metal film. See, for example, "Eddy Current", Section 1.4.1, pages 27–30, in the book by Schroder (referenced above).

Each of the above-described methods requires a metallized region having a width (e.g. 0.5 mm) that may be several orders of magnitude larger than a typical metal line's width (e.g. <0.5 microns). Due to the requirement of the metallized region to have a 1000 times larger width, the measurements are performed prior to patterning, typically on a test wafer. Moreover, the above-described methods measure merely the resistivity of a metal film, and are not known to be used in the measurement of resistance of a line formed after etching the metal film (e.g. in a production wafer).

U.S. Pat. No. 5,228,776 granted to Smith et al. (hereinafter "Smith") describes measuring changes in optical reflectivity (column 4, line 5–6) caused by thermal waves (column 3, line 42) to "monitor variations in electrical conductivity and resistance . . ." (column 4, lines 53–54). Specifically, Smith requires "periodically exciting the sample at a highly localized spot on the sample surface. . . . The pump beam functions to periodically heat the sample which in turn generates thermal waves that propagate from the irradiated spot. . . . Features at or beneath the sample surface can be studied by monitoring the variations they induce in these waves" (column 1, lines 25–40). Smith also states that "when the optical reflectivity of the sample is to be monitored, it is desirable to arrange the pump and probe beams to be coincident on the sample" (column 1, lines 60–64). When using such coincident beams, Smith notes problems created by "surfaces associated with defective vias are often not optically flat . . ." (column 3, lines 6–13). Moreover, prior art also states that "[w]hen materials other than semiconductors are to be evaluated, such as metals . . . analysis of the thermal wave patterns is required" (see U.S. Pat. No. 4,854,710 at column 7, lines 41–44).

SUMMARY OF THE INVENTION

According to the principles of the invention, an apparatus focuses a beam of electromagnetic radiation (also called "heating beam") on a region (also called "heated region") of a conductive layer such that heat generated by the beam transfers out of the heated region primarily by diffusion, i.e. by conduction under steady state conditions, thereby eliminating the creation of a thermal wave as described in U.S. Pat. No. 5,228,776.

Specifically, a method implemented by the apparatus (also called "measurement apparatus") includes (1) focusing the heating beam on the region, (2) modulating the power of the heating beam at a frequency that is predetermined to be sufficiently low to ensure that at least a majority (preferably almost all) of the generated heat transfers from the heated region by diffusion, and (3) measuring the power (also called "reflected power") of a portion of another beam (also called "probe beam"), the portion being (a) reflected by the heated region, and (b) modulated in phase with modulation of the heating beam.

In one embodiment, the above described acts (1)–(3) are repeated by the measurement apparatus between various acts in the fabrication of a substrate, at each of a number of regions on a line (formed by patterning the conductive layer), and any change in the measurements of the reflected power indicates a corresponding change in resistance (per unit length) of a conductive line. In another embodiment, the conductive layer is not patterned into a line, and instead the measurement apparatus performs the above-described acts on one or more regions of an unpatterned conductive layer, and measures the sheet resistance.

When the measurements change by more than a predetermined amount (e.g. by 10%), one embodiment of the measurement apparatus changes a process parameter that controls one of the fabrication acts (e.g. the metallization act) in a "feedback" loop to return the measurement to normal in the next wafer (or next batch of wafers). Performance of acts (1)–(3) during a fabrication process, without touching a substrate (i.e. in a non-contact manner) increases yield of the fabrication process, as compared to an off-line measurement of the resistivity of a metal film on a test substrate. Also, performance of acts (1)–(3) as described herein indicates the efficacy of patterning of the specific production substrate that is otherwise not measurable e.g. when using an unpatterned substrate (such as a test substrate).

As noted above, the measurement apparatus modulates the power of the heating beam at a frequency (e.g. 1000 Hz) that is selected to be sufficiently low to ensure that at least a majority (i.e. greater than 50%) of the generated heat is transferred out of the heated region by diffusion rather than by a thermal wave. The measurement apparatus detects the reflected power that is also modulated at the just-described frequency, for example, by using a lock-in amplifier. Moreover, the apparatus filters, prior to the measurement, any portion of the heating beam that is also reflected, for example by using (a) a silicon wafer, or (b) a narrow band filter tuned to the wavelength of the probe beam, or preferably both, thereby eliminating the need for a quarter wave plate otherwise necessary in the prior art.

In one embodiment, the measurement apparatus includes sources (such as lasers) that produce each of the heating beam and the probe beam. In addition, the measurement apparatus also includes a photosensitive element (such as a "photodiode") that is located in the path of a portion of the probe beam reflected by the heated region. The photosensitive element generates an electrical signal (e.g. a voltage level) that indicates the intensity of the probe beam portion reflected by the illuminated region. The intensity in turn indicates reflectance caused by heating. So the intensity measurement is a measure of the peak temperature in the heated region. In this embodiment the measurement apparatus also includes a computer that is coupled to the photosensitive element to receive the electrical signal, and that is programmed to determine the value of a material property in the heated region from one or more such measurements.

Use of diffusion as described herein to transfer a majority of the generated heat from the heated region is a critical aspect of the invention, and eliminates the need for a thermal wave as described above. Transferring heat by diffusion as described herein causes a conductive line to have a steady-state temperature (called "peak temperature") at the center of the heated region, and the peak temperature changes in phase with modulation of the heating beam. As the reflectance of a conductive line varies linearly with the peak temperature, the reflectance also changes in phase with modulation of the heating beam.

In a first embodiment, the measurement apparatus computes a ratio (also called "steady-state ratio") of a change in reflected power to a corresponding change in the power of the heating beam, with the probe beam power constant, and uses the ratio as a measure of the resistance of the conductive line. Specifically, the steady-state ratio when multiplied by a predetermined constant yields, per unit length, the resistance of the conductive line in the heated region. Therefore, the apparatus uses a change in the steady-state ratio as a measure of a change in the resistance of the conductive line between the heated regions.

As shown below, the reflectance obtained by heating a conductive line as described herein increases linearly with the power of the heating beam. The reflectance when plotted with respect to the power of the heating beam, yields a straight line. The slope of the straight line is the steady state ratio. This slope is approximately a product of a number of known factors and the resistance per unit length of the conductive line. Therefore, the steady-state ratio provides a measure of the resistance per unit length.

In a second embodiment, the measurement apparatus computes a ratio (also called "steady-state ratio") of the reflected power to the power of the heating beam and uses the ratio as a measure of the resistance per unit length of the conductive line. The second embodiment eliminates the need to perform at least two measurements that are otherwise required to determine a straight line, and is based on the fact that the reflected power is zero when the power of the heating beam is zero (i.e. uses origin as one of the points on the straight line described above). Note that in one implementation, a steady state ratio is not computed, and instead a measurement of the difference in reflected powers in the presence and absence of a heating beam is used directly as a measure of the resistance of a line, e.g. when using a heating beam having unit power.

Determination of a steady-state ratio (as described above) during the fabrication of a substrate (e.g. immediately after patterning) provides an accurate indication of a change in resistance of a conductive line across the various regions of the wafer. Specifically, monitoring the steady-state ratio identifies an increase in a conductive line's resistance e.g. due to voids or due to impurities segregated at grain boundaries both of which cannot be detected by visual inspection methods. Moreover, use of a steady-state ratio as a measure of a conductive line's resistance detects not only variations in resistivity, but also variations in thickness and in width of the conductive line.

Also, a difference in reflectance measurements as described herein identifies a change in a property of a material other than the material of the conductive line. For example, a change in adhesion between a conductive line and an underlying insulation layer causes a corresponding change in the dissipation of heat from the conductive line through the underlying layer, and is detected as a change in the reflectance measurement. Moreover, such a difference in reflectance measurement also indicates a change in thermal conductivity of the underlying layer, e.g. due to a change in porosity or density of the layer. Specifically, the lower the thermal conductivity of the insulation layer, the higher the temperature of the conductive line (assuming the average power of the heating beam stays the same).

Such a change in thermal conductivity also indicates a corresponding change in the dielectric constant of the underlying material. Also, a change in the dielectric constant can indicate a change in the capacitance between the conductive line and one or more adjacent conductors or the ground plane. The change in capacitance in turn indicates a change in the speed of transmission of signals in the integrated circuit.

Note that the substrate that supports a conductive layer or a conductive line can be any of the following: a silicon wafer that is processed to form integrated circuit dice, a glass plate that is processed to form a liquid crystal display or a resin (such as BT) core that is processed to form a printed circuit board.

DETAILED DESCRIPTION

Figure 1A:
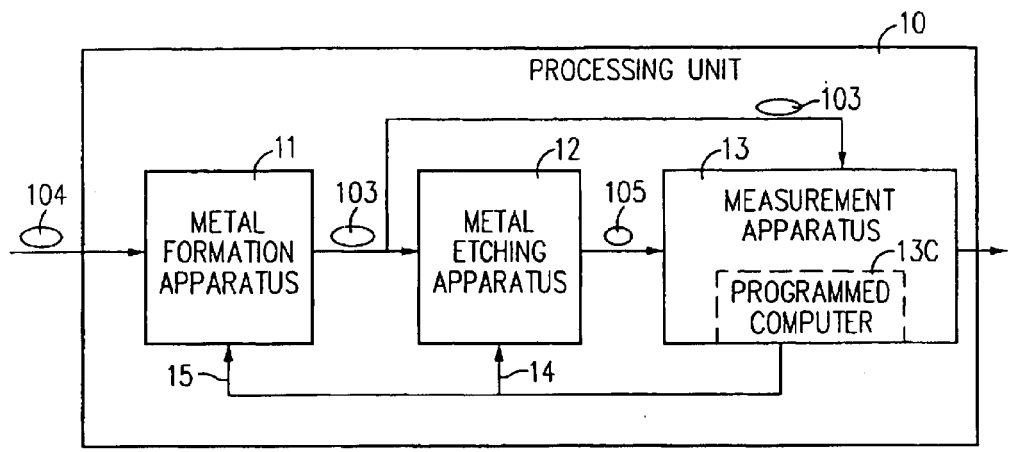
FIG. 1A illustrates, in a block diagram, use of one embodiment of a measurement apparatus of this invention with a metal formation apparatus for forming a conductive layer and a metal etching apparatus for patterning the conductive layer.

A processing unit 10 (FIG. 1A) can be operated in accordance with the invention to create integrated circuit (abbreviated as "IC") dice by processing a substrate 104 to form a patterned substrate 105, measuring the resistance of one or more conductive lines in patterned substrate 105, and adjusting the processing in real time if necessary. Specifically, unit 10 includes a metal deposition apparatus 11 that forms on substrate 104 a layer of conductive material (such as a metal) to form a metallized wafer 103 that is in turn processed by metal etching apparatus 12 that etches the film to form one or more conductive lines in substrate 105. Unit 10 also includes a resistance measurement apparatus 13 that measures the resistance of one or more of the conductive lines (e.g. line 111 in FIG. 1B) on patterned substrate 105, or of one or more regions on unpatterned substrate 103 or both (i.e. before and after patterning of the same substrate).

If the resistance measurement falls outside of the specifications for a substrate 103 or 104, a process parameter can be adjusted by resistance measurement apparatus 13. One embodiment of apparatus 13 includes an optional programmed computer 13C that drives an active signal on line 14 that is coupled to metal etching apparatus 12, or on line 15 that is coupled to metal formation apparatus 11, or both, depending on the measurement. A change in the process parameter can be determined automatically by software in programmed computer 13C, or can be entered by a human operator.

In one embodiment, an unpatterned substrate 103 is transferred to resistance measurement apparatus 13 for measurement of a property of a conductive layer formed thereon. Examples of such a property are conductivity and thickness as described below in reference to FIGS. 8A, 8B and 9. Such an intermediate measurement provides a more immediate feedback to control the operation of metal formation apparatus 11 as compared to an otherwise long delay (several hours or days) between forming a conductive layer and etching a pattern.

Resistance measurement apparatus 13 determines, between acts of fabricating unpatterned substrate 104 or patterned substrate 105 (FIG. 1B), a measure of the electrical resistance by use of two coincident beams 101 and 102 of electromagnetic radiation (such as laser beams). A first beam (also called "heating beam") 101 has a power (also called "heating power") that is modulated at a predetermined frequency. A second beam (also called "probe beam") 102 is continuous, and is weaker than first beam 101. First beam 101 is incident on and heats a region 111R on substrate 104 or 105 to a temperature T, and second beam 102 is reflected by region 111R in phase with modulation of first beam 101, because temperature T is modulated in phase with modulation of first beam 101.

Figure 2:
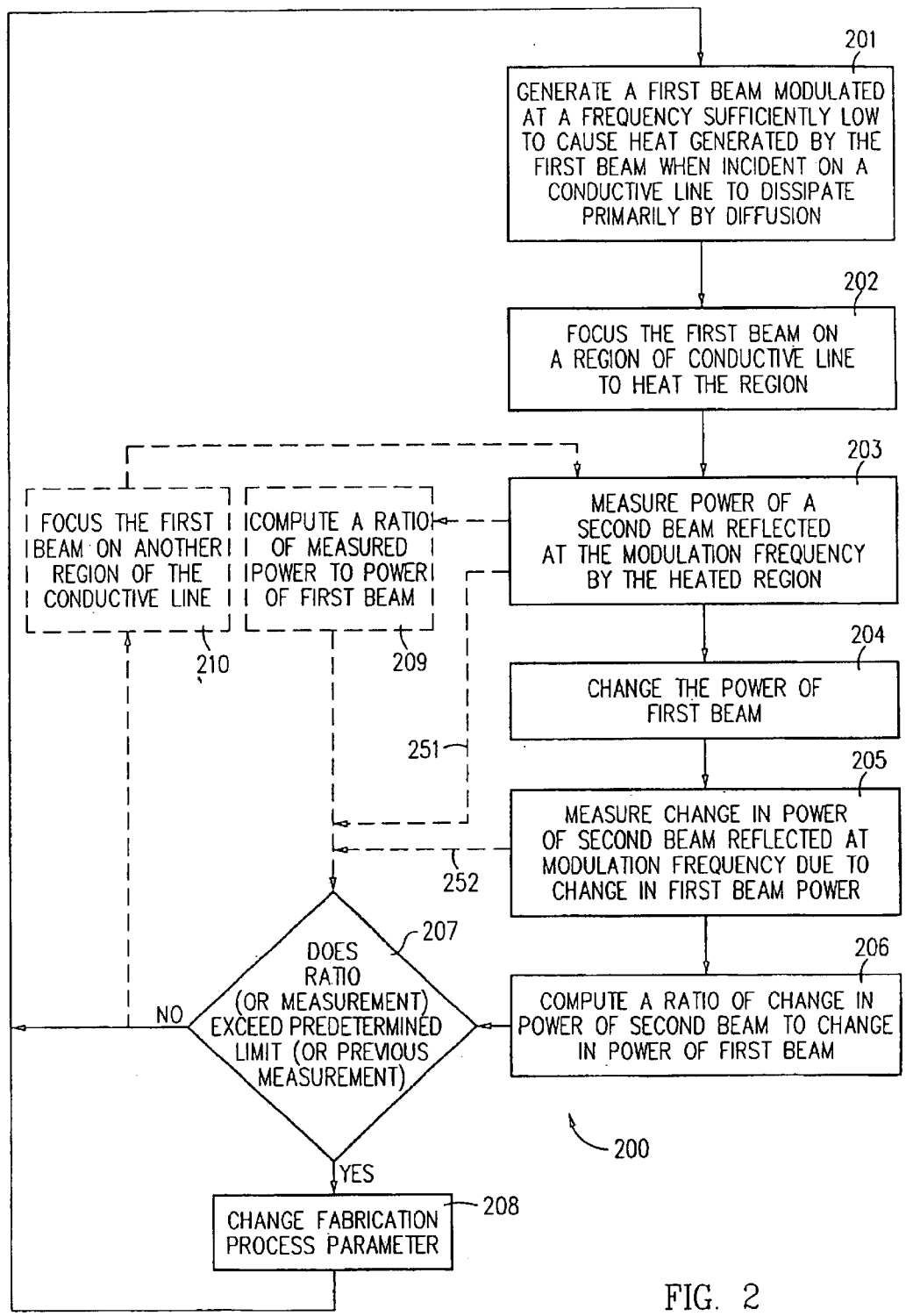
FIG. 2 illustrates, in a flow diagram, a method for using the two beams of FIG. 1B to measure a change in resistance of conductive line 111, and use of the measurement to control the processing of wafers by the metal formation apparatus and metal etching apparatus in FIG. 1A.

The predetermined frequency of modulation of first beam 101 is selected to be sufficiently small to ensure that a majority (i.e. greater than 50%) of heat generated by first beam 101 flows by diffusion out of heated region 111R (e.g. along the length L of line 111 on substrate 105). In one embodiment, the predetermined frequency is selected to cause substantially all (e.g. greater than 90%) of heat generated by first beam 101 in region 111R to be transferred to adjacent regions 111S and 111T by diffusion. Such a diffusive heat transfer allows the use of a diffusion equation solution (20) as described below to relate electrical and thermal conductivity in a measurement method 200 (FIG. 2). Therefore, the predetermined frequency is selected to be lower than a maximum frequency beyond which the effects of a thermal wave become noticeable. The maximum frequency is inversely related to a dimension of heated region 111R (e.g. the length L) as described below in reference to equation (11). In one embodiment, length L is approximately 100 microns, and the maximum frequency is 1430 Hz for copper lines, and 1080 Hz for aluminum lines.

Note that the following discussion makes a specific reference to a conductive line 111, although as noted later (in reference to FIGS. 8A, 8B and 9) a similar analysis in applicable to a portion of a conductive layer. Moreover, although the following description refers to a wafer of silicon (such as wafer 103, 104, or 105), the description is equally applicable to any substrate that supports a conductive layer, and other examples of such a substrate include a glass plate and a resin core. For convenience, the same reference numerals are used for a wafer and a substrate.

The diffusion of heat from region 111R creates a temperature profile 150 (FIG. 1C) in conductive line 111, with a hottest point C (having a peak temperature $T_p$) located at the center of region 111R under the following assumption. In one example, conductive line 111 is supported on a dielectric layer 112 (FIG. 1B) of a wafer 105 having a thermal conductivity $K_i$ that is almost two orders of magnitude lower than the thermal conductivity $K_m$ of conductive line 111. Note that such a large difference in thermal conductivities is not required for the relation in equation (20) described below. Instead, equation (20) holds as long as the thermal conductivity $K_i$ of dielectric layer 112 is smaller than the thermal conductivity Km of line 111.

Peak temperature $T_p$ (FIG. 1C) is a function of the thermal conductivity $K_m$ and the cross-sectional area $Wh_m$ of conductive line 111, wherein W is width and $h_m$ is height of line 111. As the electrical and thermal conductivities are related (as shown in equation (1)), peak temperature $T_p$ indicates (as discussed more completely below), per unit length, conductive line 111's electrical resistance.

Temperature profile 150 has substantially the same "bell" shape (FIG. 1B) over length L at any time during a cycle at the predetermined frequency. Therefore, temperature T is modulated without forming a wave in space (in a manner analogous to direct current ("DC")) during the cycle. Temperature T is modulated only to increase the accuracy in measurement, specifically the signal-to-noise ratio (described below in reference to equation 21) by use of synchronous detection of a portion of probe beam 102 reflected by region 111R. Moreover, the predetermined frequency can be arbitrarily low, limited only by the minimum throughput required of the fabrication process.

Figure 1B:
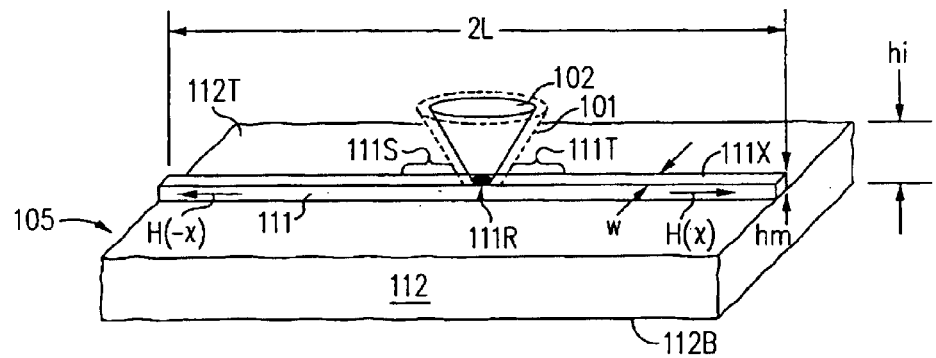
FIG. 1B illustrates, in the apparatus of FIG. 1A, a heating beam focused on a region 111R of a conductive line 111 under steady state conditions while a probe beam is used to measure reflectance of region 111R.
Figure 1C:
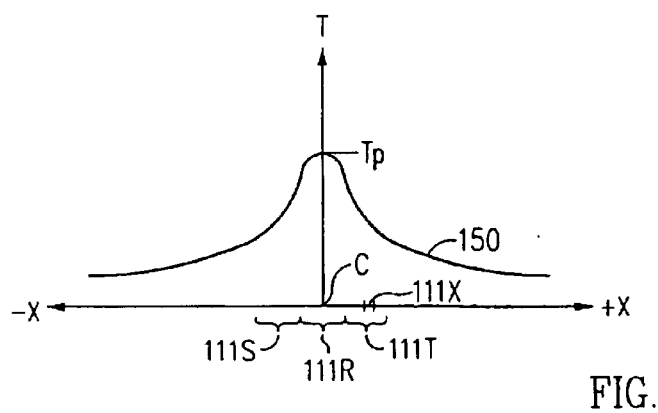
FIG. 1C illustrates, in a graph, the temperature of heated region 111R and of adjacent regions 111S and 111T in the conductive line of FIG. 1B.

In one embodiment, a measure of the electrical resistance of line 111 is determined by performing acts 201–206 of a method 200 (FIG. 2). Specifically, in act 202, heating beam 101 is focused on a region 111R (FIG. 1B). In act 201 (FIG. 2), the power of heating beam 101 is modulated at the predetermined frequency. Note that acts 201 and 202 can be performed in reverse order, i.e. act 202 performed first followed by performance of act 201.

Next, the power (also called "reflected power") of probe beam 102 after reflection by region 111R is measured in act 203. Thereafter, in act 204, the power of heating beam 101 (FIG. 1B) is changed, e.g. increased from 1 milliwatt to 5 milliwatts. Next, in act 205 (FIG. 2), a change in the reflected power in response to the change in power of heating beam 101 is determined. Thereafter, in act 206, a ratio of the change in reflected power to the change in power of heating beam 101 is computed. The ratio indicates, per unit length, a measure of the electrical resistance of conductive line 111 in region 111R. Note that during the just-described operations, the power (also called "probe power") of probe beam 102 that is incident on region 111R remains constant in this embodiment. The ratio may itself be compared (in act 207) with a predetermined limit to check if line 111 is within specifications and if so, return to act 201 (for another wafer).

The ratio (also called "steady-state ratio"), when multiplied by a predetermined constant yields, per unit length, the resistance of conductive line 111 in heated region 111R. As described more completely below, the constant's value is determined (see equation (20)) by a number of factors, such as absolute reflectance $R_o$ of the conductive line 111 in heated region 111R, dielectric constant of free space $\epsilon_0$, frequency of modulation $v_L$ of the reflected portion of probe beam 102, Boltzmann's constant $k_B$, electron charge q, ambient temperature $T_o$, rate of change of resistivity with temperature, and power of probe beam 102, as well as the thickness $h_i$ and thermal conductivity $K_i$ of insulating layer located underneath the conductive line. The steady-state ratio when multiplied by such a constant yields $(\rho_e/Wh_m)$ where $\rho_e$ is the resistivity, W is the width of conductive line 111 and $h_m$ is the thickness of conductive line 111.

In one implementation, heating beam 101 is focused (in act 210) in another region (e.g. region 111T) and the measurement is repeated (in act 203), and the two measurements are compared. Any reduction in width W or height $h_m$ results in an increase in the steady-state ratio that can be detected by the comparison. Similarly, any increase in resistivity also increases the steady-state ratio, and is also detected by the just-described comparison. Furthermore, a problem in adhesion of conductive line 111 to the underlying dielectric layer 112 (e.g. due to voids or delamination) also causes an increase in the steady-state ratio and is therefore also detected by the comparison.

In one implementation, the above-described measurements (either a single measurement or two or more measurements per region) are repeated after focusing (see act 210) heating beam 101 in each of three different regions that define a triangular area on conducive line 111. Instead of comparing numerical measurements, a change in the steady state ratio can be detected by plotting a graph of the steady state ratio as a function of distance.

Therefore, the event of a change in the steady-state ratio (e.g. exceeding a predetermined limit) provides an indication that the fabrication process has changed, and that conductive line 111 is no longer within the specification. In response to the indication, an operator or an appropriately programmed computer changes a process parameter that controls the fabrication of line 111 (see act 208 in FIG. 2) and that changes the process to return a conductive line in the next wafer to within the specification. For example, the operator identifies a source of contamination in metal formation apparatus 11 (FIG. 1A) that degrades the resistivity of a metal layer formed on wafer 103, and changes a parameter related to the source.

A steady-state ratio as described above is measured at a single spot (e.g. in region 111R), allowing the measurement (of the value of reflected power) to be made in a more compact area (e.g. a region of length 1 micron) than possible by a method that requires two locations (each displaced from the other), e.g. as disclosed in U.S. Pat. No. 5,228,776. In the just-described example, since only the power of beam 101 that is incident on line 111 heats the line, width W (FIG. 1B) of line 111 can be smaller than the diameter of beam 101 (that may have a minimum size larger than line width W). The temperature of a region 111R (of length equal to the diameter of beam 101) in line 111 that is heated under diffusive conditions as described herein is a function of the thermal properties of an extended length L (typically several tens of microns) of line 111 about the heated region 111R.

In the prior art (e.g. U.S. Pat. No. 5,228,776), the heat propagates away from a heated region in a thermal wave, and the temperature at the heated region is not a direct function of the physical properties of the conductive line at a distance. This is because a thermal wave at any point is the sum of heat from an outgoing wave and heat from waves reflected from one or more regions in the line where the metal properties have changed. This sum is difficult to quantify in the prior art, because the reflective properties of defects may not be known in advance.

In contrast, during diffusive heat transfer, the heat at any point is affected in a quantifiable manner (as described below in reference to FIG. 4B) by the reflective properties of defects or vias at a distance from the point. Also, method 200 provides an unexpected result, specifically the value of reflected power as measured by method 200 is unaffected by the presence of non-flat surfaces (that cause problems in the prior art, e.g. U.S. Pat. No. 5,228,776) because a reflectance measurement as described herein is independent of the small angular deflection that is caused by periodic undulation of a surface by passage of a thermal wave.

In one example, apparatus 13 operates heating beam 101 at 0.001 watts and at 0.002 watts and obtains intensity measurements for these two power as follows: probe beam has an incident power on heated region 111R of 1.1 milliwatts, and (1) a modulated component of reflected power of 0.55 microwatts, thereby yielding $\Delta R=(0.55/1.1)\times 10^{-3}=0.5\times 10^{-3}$; and (2) a modulated component of the reflected power of 1.1 microwatts, thereby yielding $\Delta R=(1.1/1.1)\times 10^{-3}=1\times 10^{-3}$. Therefore, the slope is $\Delta R/\Delta P=(1.0-0.5)/(0.002-0.001)\times 10^{-3}=0.5$. The value of 0.5 of the slope is thereafter used with a constant (as described below in reference to equation 20) to obtain the resistance per unit length. Note that instead of using two measurements, a single measurement (e.g. at 0.001 watts of heating beam power) can be used, e.g. by computing $\Delta R/\Delta P$ as $(0.5/0.001)\times 10^{-3}=0.5$ assuming that the $\Delta R$ is zero when $\Delta P$ is zero.

In an alternative embodiment, instead of performing acts 204–206, another ratio is computed in act 209, directly after act 203, based on the fact that a modulated component of the reflected power is zero when the power heating beam 101 is zero. Specifically, a ratio of a modulated component of the reflected power to the power of heating beam 101 is computed, and used as a measure, per unit length, of the electrical resistance of conductive line 111 in act 207. Furthermore, instead of computing the ratio, the reflected power can also be used directly (by going from act 203 directly to act 207 or by going from act 205 directly to act 207) as a measure of the electrical resistance per unit length, if power of heating beam 101 is constant for each of a number of measurements for the corresponding regions e.g. regions 111R–111T.

Use of steady-state conditions as described herein eliminates the need for a generation beam having the high modulation frequency required by U.S. Pat. No. 5,228,776 to set up a thermal wave. Specifically, the above-described method eliminates the need to generate a beam modulated at a frequency in the range of 1 MHz to 100 MHz, and instead requires a beam modulated at a frequency that is several orders of magnitude smaller, e.g. in the range of 0.01 KHz to 1 KHz, thereby eliminating the thermal wave.

Figure 3:
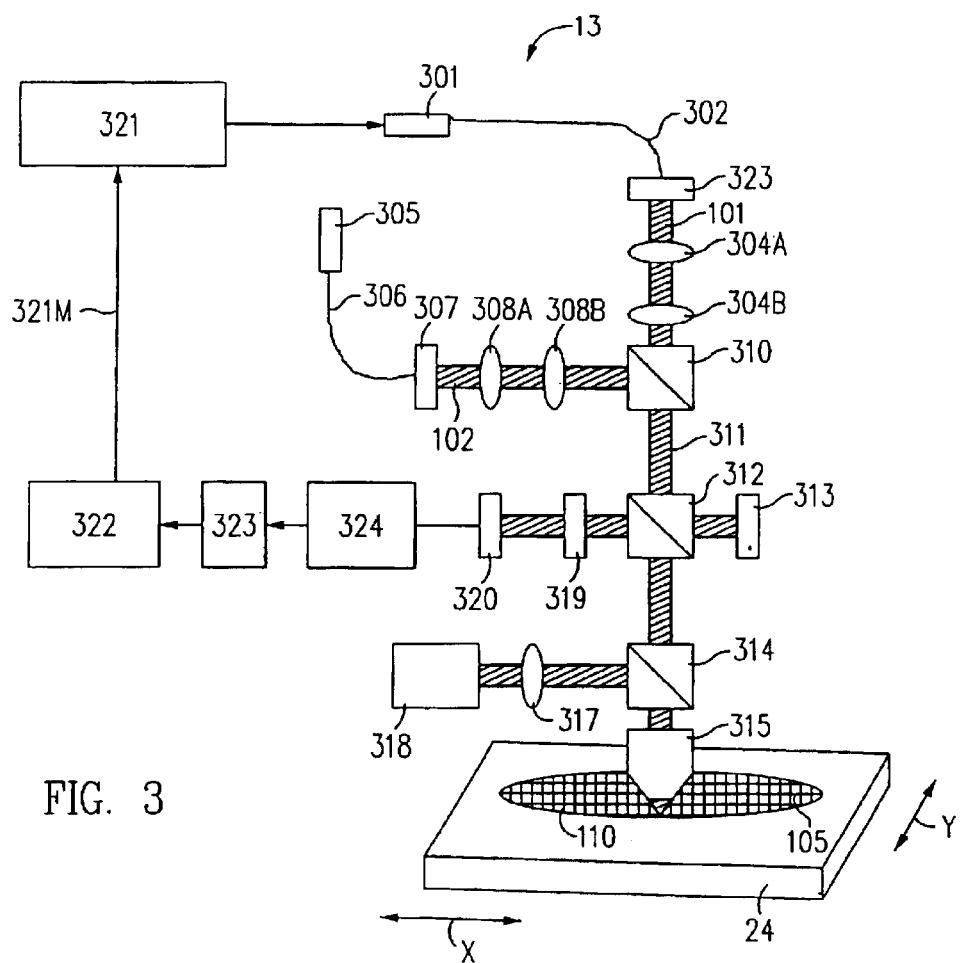
FIG. 3 illustrates, in a block diagram, a measurement apparatus that performs the method illustrated in FIG. 2.

Acts 201–206 of method 200 can be performed by use of a resistance measurement apparatus 13 (FIG. 3) having two lasers that create the two beams 101 and 102. Specifically, apparatus 13 includes a laser 301 for creating a beam 101 of electromagnetic radiation at a predetermined wavelength, such as infrared light, ultraviolet light, X-rays, gamma rays, or radiation in the microwave or radio frequencies. In a preferred embodiment, laser 301 is a AlGaAs diode laser that emits electromagnetic radiation of wavelength 830 nm.

The electromagnetic radiation created by laser 301 is transmitted through an optical fiber 302 to a collimator 323 that emits heating beam 101. In one implementation, heating beam 101 has a maximum power of, for example, 100 milliwatts. Apparatus 13 also includes lenses 304A and 304B that adjust the size of beam 101 to fill the aperture of an objective lens 315 also included in apparatus 13.

Apparatus 13 further includes a second laser 305 that creates a beam 102 of electromagnetic radiation used to measure a change in reflectance of region 111R (FIG. 1B) in response to change in power of heating beam 101. In one implementation, laser 305 is an InGaAs diode laser that emits electromagnetic radiation of wavelength 1480 nm. The electromagnetic radiation created by laser 305 is transferred by an optical fiber 306 to another collimator 307 also included in apparatus 13. Collimator 307 emits probe beam 102 having a maximum power of, for example, 7 milliwatts. Therefore, probe beam 102 has a power that is an order of magnitude smaller than the power of heating beam 101, so that conductive line 111 is not noticeably heated by probe beam 102.

Apparatus 13 also includes lenses 308A and, 308B that adjust the size of probe beam 102 to fill the aperture of objective lens 315 (described above). Apparatus 13 also includes a dichroic beam splitter 310 that combines heating beam 101 and probe beam 102 to form a combined beam 311. Combined beam 311 passes through beam splitters 312 and 314 that are also included in apparatus 13, to an objective lens 315. Objective lens 315 can be, for example, a 0.9 NA, 100 X objective lens available from Nikon of Yokohama, Japan. A portion of combined beam 311 is deflected to a photodetector 313, such as part number J16-8SP-RO5m-HS from EG&G Judson of Montgomeryville, Pa., USA. Photodetector 313 is used to verify the alignment of combined beam 311 with respect to wafer 105, and to measure the incident power of one or both of beams 101 and 102.

Light reflected from wafer 105 passes back through objective lens 315 and through beam splitter 312. Beam splitter 312 sends 50% of the reflected light through a filter 319 to a photodetector 320. Filter 319 is a narrow band filter that removes the reflected portion of heating beam 303 while passing the reflected portion of probe beam 309. Thereafter, photodetector 320 senses the intensity of the reflected portion of probe beam 309, and passes a voltage signal to amplifier 324.

Amplifier 324 converts the voltage signal into a current signal and passes the current signal to a lock-in amplifier 322. Lock-in amplifier 322 includes an oscillator as a frequency source that is used to detect the power of the reflected portion of probe beam 102 modulated at the predetermined frequency. The frequency source in lock-in amplifier 322 also provides a frequency signal on a line 321M to a laser driver 321. Laser driver 321 uses the frequency signal on line 321M to drive laser 301 at the predetermined frequency that is sufficiently low to modulate the amplitude of heating beam 303 to ensure heat transfer by diffusion as described herein.

Apparatus 13 also includes a beam splitter 314 that diverts 10% of combined beam 311 to a focusing lens 317 and a camera 318. Camera 318 is used to observe beams 101 and 102 (FIG. 1B) on wafer 105, in order to focus combined beam 311 (FIG. 3) within region 111R (FIG. 1B) on wafer.

Figure 4A:
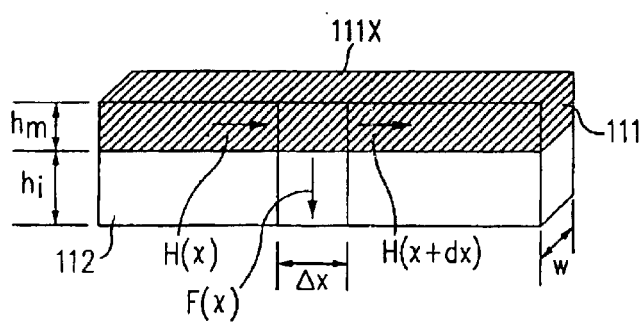
FIG. 4A illustrates the transfer of heat through a portion 111X (of region 111T in FIGS. 1B and 1C) and into dielectric layer 112 by diffusion under steady state conditions.

The above-described method 200 uses one or more of the following relationships (under steady-state conditions) between conductive line 111's thermal conductivity, electrical resistance, and reflectance to provide a non-destructive yet reliable method for detecting changes in the resistance of line 111. Specifically, the electrical resistance of conductive line 111 (FIG. 4A) is determined using the Wiedermann-Franz equation $$K_m = \left[\frac{\pi^2}{3}\left(\frac{k_B}{q}\right)^2\right]T\sigma_e \quad (1)$$

where Km is the thermal conductivity of line 111 in units of watts/(cm-deg C), σe is the electrical conductivity of line 111 in units of (ohm-cm)$^{-1}$, T is the absolute temperature of line 111, q is the electron charge, and $k_B$ is Boltzmann's constant.

The electrical resistivity of line 111 is the inverse of the electrical conductivity, $\rho_e = 1/\sigma_e$, in units of ohm-cm. The electrical resistance of line 111 is found by multiplying the electrical resistivity $\rho_e$ by L/A, where A is the cross-sectional area Wh$_m$ Wh$_m$ (FIG. 1B) in units of centimeters squared and L is the length of conductive line 111 in centimeters.

The electrical resistivity of conductive line 111 is related to the reflectance R of line 111 (a ratio of reflected power to the incoming power) by the Hagen-Rubens relation:

$$R(T) = 1 - 2\sqrt{4\pi\epsilon_0 v_L \rho_e} \quad (2)$$

where $v_L$ is the frequency (in units of cycles per second) of the reflected portion of probe beam 102 (equal to c/λ, where c is the speed of light, 3×10$^{10}$ cm/sec, and λ is the wavelength of probe beam 102). Although the above equation (2) does not strictly hold at near-infrared wavelengths (e.g. wavelengths in the 0.75 to 2 μm range, corresponding to frequencies 1.5 to 4×10$^{14}$ Hz) for good conductors such as aluminum and copper, the imaginary part of the index of refraction greatly exceeds (e.g. by an order of magnitude) the real, and the approximations used to derive equation (2) hold approximately.

Hence, conductive line 111's reflectance R is directly related to electrical resistivity $\rho_e$ and thermal conductivity $K_m$ by equations (1) and (2). Therefore, use of a heating beam 101 introduces a known heat flux Q into line 111, thereby to heat line 111 to a peak temperature $T_p$ that is determined by measuring the reflectance R of probe beam 102. Line 111's electrical resistivity $\rho_e$ is then deduced directly from equation (2).

Alternatively, as discussed below a solution of a heat-flow equation (3) yields line 111's thermal conductance per unit length as a function of temperature T, thereby yielding line 111's electrical conductance per unit length and its inverse, the electrical resistance per unit length. The analysis provided below uses the following assumptions. Heat flux $H_{out}(x)$ flowing into a region of width Δx around a point 111X (FIG. 4A) outside of region 111R (FIG. 1B) in line 111 is diffusive and hence temperature profile 150 (FIG. 1C) has a static solution rather than wave-like solution. Conductive line 111 (FIG. 1B) is a conductor that has a length L assumed to be infinite along the X axis (as compared to the diameter of heated region 111R). Moreover, conductive line 111 has thermal conductivity $K_m$, and lies on an insulation layer 112 with a thermal conductivity $K_i$ and thickness $h_i$. The light from heating beam 101 that is not reflected is fully absorbed by line 111, creating a heat flux H (FIG. 1B) flowing in both the positive and negative X directions from heated region 111R.

Initially assume that heat flow F(x) into insulation layer 112 is small compared to flow H(x) along line 111—an assumption that is valid when the thermal conductivity of line 111 is much greater than the thermal conductivity of layer 112. The temperature T at any point 111X (FIG. 1C) along conductive line 111 is found by solving the one-dimension heat diffusion equation for the difference in temperature T between line 111 and the ambient:

$$\frac{\partial^2 \Delta T}{\partial x^2} - \frac{1}{\kappa_m}\frac{\partial \Delta T}{\partial t} = 0 \quad (3)$$

The first term in equation (3) represents the diffusion of heat, which creates a static distribution. The second term represents the time-variation of the temperature, giving rise to the wave-like solution. The units of $K_m$ are watts/(cm-deg. C.). The thermal diffusivity $K_m$ is related to the thermal conductivity $K_m$ as $K_m = K_m/\rho_m C_m$, where $\rho_m$ is the density of line 111 (in units of gms/centimeter$^3$) and $C_m$ is the heat capacity (in units of Joule/gm-degree C.) of line 111

Equation (3) is solved by separation of variables. Assume a time-dependent solution for temperature T of line 111 of the form $$\Delta T(x, t) = u(x)e^{j\omega t} \quad (4)$$

where ω is the modulation frequency. Substituting (4) into (3) gives an equation in x, $$\frac{\partial^2 u(x)}{\partial x^2} - j\frac{\omega}{\kappa}u(x) = 0 \quad (5)$$

The solution that is finite at infinity is $$u(x) = A\exp\left(-x\sqrt{j\frac{\omega}{\kappa}}\right) = A\exp\left(-x(1+j)\sqrt{\frac{\omega}{2\kappa}}\right) \quad (6)$$

Combining (4) and (6), the temperature as a function of position and time is $$\Delta T(x,t) = Ae^{-kx}\cos(\omega t - kx) \quad (7)$$

where $$k = \frac{2\pi}{\lambda} = \sqrt{\frac{\omega}{2\kappa_m}} \quad (8)$$

A is a constant determined by the initial conditions, and ω is radial frequency of the thermal wave.

Equation (7) is a wave solution, with a frequency f=ω/2π and a wavelength λ given by equation (8). If the wavelength λ of the thermal wave is long compared to the dimensions of the measurement, then k in equation (8) will be small. If k is sufficiently small, the second term in equation (5)—representing the time dependence—will be insignificantly small (e.g. less than 1%) compared to the static derivative term. The assumption that k is small reduces equation (5) to $$\frac{\partial^2 u(x)}{\partial x^2} = 0 \quad (9)$$

Equation (9) has no time dependence, and is a steady state equation for transfer of heat by diffusion, identical to equation (3) when d(ΔT)/dt=0 (with insignificant variation of ΔT with respect to time).

Assume L (FIG. 1B) is the length of line ill over which heat diffuses to set up the steady state temperature distribution upon which the measurement is based. The condition for a steady state solution is that measurement length L must be negligibly small compared to the thermal wavelength:

$$\lambda = 2\pi \sqrt{\frac{2\kappa_m}{\omega}} \gg L \qquad (10)$$

Using a factor of 10 (i.e. one order of magnitude) to signify "very much greater than", the equation for the modulation frequency is $$f = \frac{2\pi}{\omega} < \frac{\pi \kappa_m}{25 L^2} \qquad (11)$$

The table below gives the relevant constants and the thermal wavelength λ at 1000 Hz for various materials.

| Material | ρ<br>g/cm3 | C<br>J/g-K | K<br>W/cm-K | κ<br>cm²/sec | λ @ 1 KHz<br>µm |
|---|---|---|---|---|---|
| Aluminum | 2.70 | 0.90 | 2.37 | 0.98 | 1105 |
| Copper | 8.96 | 0.39 | 3.98 | 1.14 | 1197 |
| Tungsten | 19.3 | 0.14 | 1.79 | 0.66 | 911 |
| Silicon | 2.328 | 0.70 | 1.45 | 0.89 | 1058 |

For the above values and length of measurement L of 100 microns, the steady-state approximation requires a modulation frequency of less than a maximum frequency of, e.g. 1430 Hz for copper and 1080 Hz for aluminum.

The maximum frequency is also inversely related to the distance over which the temperature T decays to, e.g. 10% of the peak temperature $T_p$. If such a distance (also called "decay distance") is smaller than measurement length L, the maximum frequency can be higher than the just-described maximum frequency. For example, if the decay distance is 20 microns, the maximum frequency is 5985 hz for copper and 5525 hz for aluminum.

Temperature profile 150 (FIG. 1C) is determined by solving the static heat equation for region 111R (FIG. 1B), taking into account heat loss into insulation layer 112. Assume a region (not labeled) around point 111X (FIG. 4A) of conductive line 111 has a length Δx, a width w, and a thickness $h_m$. Insulation layer 112 has thickness $h_i$ and thermal conductivity $K_i$, and is assumed to be at the temperature of conductive line 111 at top surface 112T, and at the ambient temperature at the bottom surface 112B.

Heat flux H(x) is primarily along conductive line 111, but a small amount of heat F(x) leaks through insulation layer 112. By conservation of energy, H(x)=F(x)+H(x+dx), assuming negligible loss (less than 1%) to convection and radiation. Such losses may be included as additional terms added to the loss F(x) due to heat flow into insulator 112, (especially for convection, which scales as the temperature difference between the ambient and the insulator, as does the loss into the insulator). The diffusive heat flux is given by the derivative of the temperature times the thermal conductivity. Across the thickness $h_i$ of insulation layer 112 the derivative is approximately $T(x)/h_i$, giving $$-K_m w h_m \frac{dT}{dx}\bigg|_x = -K_m w h_m \frac{dT}{dx}\bigg|_{x+\Delta x} + \frac{K_i w \Delta x T}{h_i} \qquad (12)$$

in the limit as dx approaches zero, equation (12) reduces to the equation for the temperature distribution in the metal under the condition of diffusive heat flow, $$\frac{d^2 T}{dx^2} - \frac{K_i}{K_m} \frac{T}{h_m h_i} = 0 \qquad (13)$$

Solving equation (13) subject to the boundary conditions of ambient temperature at infinity and an incident flux $(1-R)P_L/2$, where $P_L$ is the heating laser power, R is the metal reflectance, and the factor of 2 arises because heat flows in both the +x and −x directions, gives the temperature distribution as a function of the laser power and material constants, $$T(x) = T_0 + \frac{(1-R)P_L}{2 w h_m} \sqrt{\frac{h_m h_i}{K_m K_i}} \exp\left[-\frac{x}{K_m}\sqrt{\frac{K_m K_i}{h_m h_i}}\right] = T_0 + \Delta T(x) \qquad (14)$$

The thermal conductivity of insulation layer 112 is typically about 1% of conductive line 111. For insulation layer 112 having a thickness $h_i$ of 1 µm, and a metal layer of equal thickness, the temperature drops to 1/e in about 10 microns. This is well under the condition of 100 microns line length assumed above. For example, a laser power of 0.005 W on a 0.25 µm ×0.5 µm when shone on an aluminum line, with a reflectance of 90%, yields a temperature rise of 35 degrees C.

Figure 5:
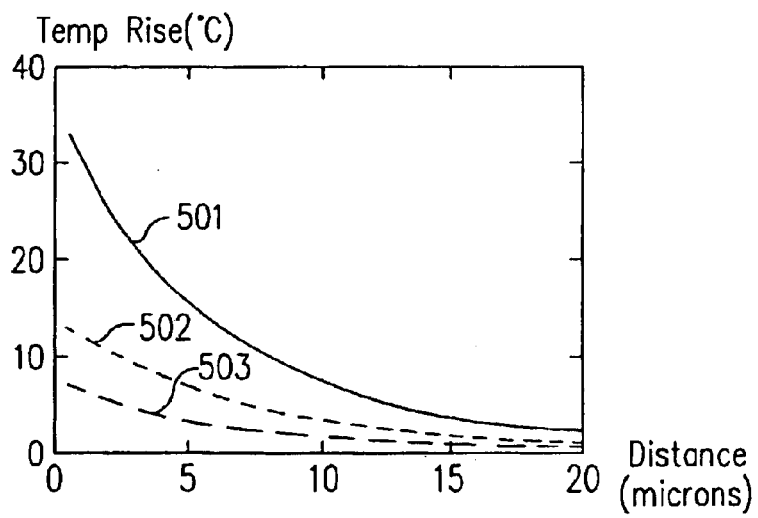
FIG. 5 illustrates, in a graph, the rise (above ambient) of temperature in ° C. of conductive line 111 (FIG. 4A) as a function of power levels (of 5, 2 and 1 mw for respective lines 501–503) of a heating beam that illuminates region 111R of FIG. 1B.

Lines 501–503 (FIG. 5) illustrate the temperature rise for various powers (also called "reflected power") reflected by line 111 (FIG. 1A) in one exemplary wafer 105. In the examples of FIG. 5, line 111 has a width w of 0.25 µm, and a thickness $h_m$ of 0.5 µm, and is formed of aluminum on a dielectric layer 112 formed of silicon dioxide and having a thickness hi of 1 µm. For the following analysis, conductive line 111 is assumed to be on an insulation layer 112 having a thermal conductivity equal to 1% of the thermal conductivity of conductive line 111.

The Wiedemann-Franz law, equation (1), is used to express the change in temperature ΔT in line 111 as a function of the metal resistivity, $$\Delta T(x=0) = \left(\frac{q}{\pi k_B}\right)\left(\frac{(1-R)P_L}{2 w h_m}\right)\sqrt{\frac{3 h_m h_i \rho_e}{K_i T_0}} \qquad (15)$$

The Hagen-Rubens relation, equation (2), is used to relate the change in temperature to the reflection, $$R(T) = \qquad (16)$$
$$1 - 2\sqrt{4\pi\varepsilon_0\left(\frac{c}{\lambda}\right)\rho_e(T)} \approx 1 - 2\sqrt{4\pi\varepsilon_0\left(\frac{c}{\lambda}\right)\rho_e(T_0)}\left(1 + \frac{\Delta T}{2\rho_e(T_0)}\frac{d\rho_e}{dT}\right)$$

where the Taylor series expansion of the resistivity has been used, $$\rho_e(T) = \rho_e(T_0) + (T-T_0)\frac{d\rho_e}{dT} = \rho_e(T_0) + \Delta T \frac{d\rho_e}{dT} \qquad (17)$$

Substituting equation (15) into (16), gives the reflectance in terms of the derivative of the resistivity with respect to temperature. The following terms in equation (16), $$1 - 2\sqrt{4\pi\varepsilon_0\left(\frac{c}{\lambda}\right)\rho_e(T_0)}$$

do not vary with the modulation of the heating laser. The third term, in equation (16)

$$2\sqrt{4\pi\varepsilon_0\left(\frac{c}{\lambda}\right)\rho_e(T_0)}\left(\frac{\Delta T}{2\rho_e(T_0)}\frac{d\rho_e}{dT}\right)$$

varies with the modulation, and can be measured using synchronous detection. This third term is used to find a change in reflectance, $$\Delta R = \sqrt{4\pi\varepsilon_0 \frac{c}{\lambda} \left(\frac{q}{\pi k_B}\right)\left(\frac{(1-R)P_L}{4wh_m}\right)}\sqrt{\frac{3h_m h_i}{K_i T_0}} \frac{d\rho_e}{dT} \quad (18)$$

where the frequency of the probe light in terms of its wavelength $\lambda$ is $v=c/\lambda$, where c is the speed of light.

From the Bloch-Grueneisen law, the temperature dependence of resistivity varies as $$\rho(T) = \rho(T_\theta)\left(.92\frac{T}{T_\theta} - .13\right) \quad (19)$$

where $T_\theta$ is the Debye temperature (333 degrees Kelvin for aluminum and 395 degrees Kelvin for copper). Relation (19) holds for $T/T_\theta > 0.25$, and is generally valid at or above room temperature for the metals of interest in fabrication of wafers.

Taking the derivative of equation (19) and substituting into equation (18) gives the relation between the reflection and the resistance per unit length, $\rho_e/wh_m$, $$\Delta R = \sqrt{4\pi\varepsilon_0 \frac{c}{\lambda} \left(\frac{q}{\pi k_B}\right)\left(\frac{(1-R)P_L}{4}\right)}\sqrt{\frac{3h_m h_i}{K_i T_0}} \left(\frac{.92}{T_\theta}\right)\left(\frac{\rho_e(T_\theta)}{Wh_m}\right) \quad (20)$$

Equation (20) is the governing equation of operation for act 206 of method 200 described above. The measurements indicative of resistance are carried out as follows: the amplitude of the reflected portion of probe beam 102 at the modulation frequency is measured as a voltage level and is converted using a calibration constant into reflectance (apparatus 13 is calibrated using samples having known reflectance to obtain a scaling factor that when multiplied with a measured voltage level yields the reflectance). The reflectance is then plotted (see line 601 in FIG. 6) as a function of the power of heating beam 101. The slope ($\Delta R /\Delta P$) of the resulting line 601 provides a value of the following partial product in equation (20) that includes everything but the power $P_L$ of heating beam 101:

$$\sqrt{4\pi\varepsilon_0 \frac{c}{\lambda}} \left(\frac{q}{\pi k_B}\right)\left(\frac{(1-R)}{4}\right)\sqrt{\frac{3h_m h_i}{K_i T_0}} \left(\frac{.92}{T_\theta}\right)\left(\frac{\rho_e(T_\theta)}{wh_m}\right)$$

The above partial product contains all known parameters except for resistance per unit length, $\rho_e/Wh_m$ at the Debye temperature $T_\theta$. Therefore, the resistance per unit length $\rho_e/Wh_m$ is found by dividing the slope ($\Delta R /\Delta P$) (also called "steady state ratio" and obtained as described above) with the following constant:

$$\sqrt{4\pi\varepsilon_0 \frac{c}{\lambda}} \left(\frac{q}{\pi k_B}\right)\left(\frac{(1-R)}{4}\right)\sqrt{\frac{3h_m h_i}{K_i T_0}} \left(\frac{.92}{T_\theta}\right)$$

Figure 6:
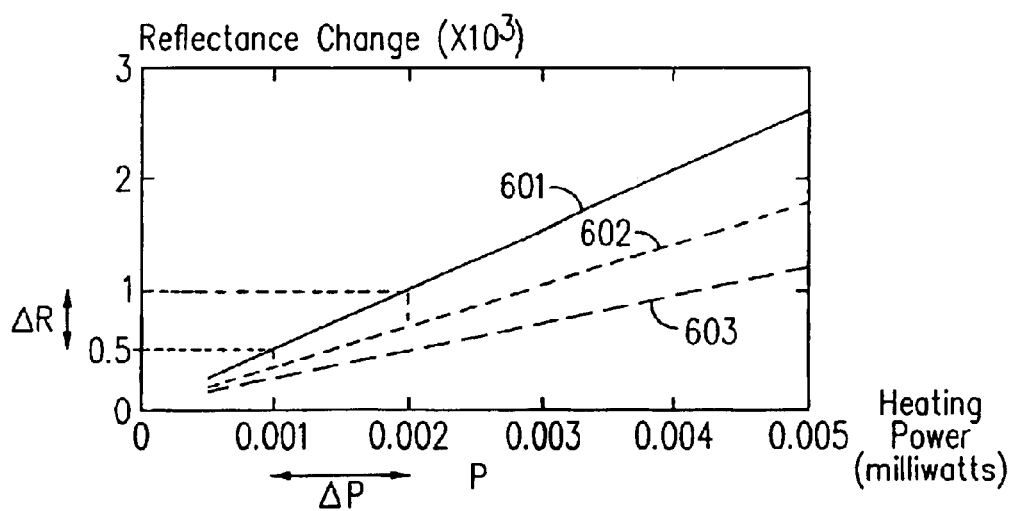
FIG. 6 illustrates, in a graph, a change in reflectance (plotted along y axis after scaling by a factor of 1000) of conductive line 111 (FIG. 4A) as a function of the powers of a heating beam as described above in reference to FIG. 5 for various thicknesses (of 0.2, 0.5 and 1.0 $\mu$m for lines 601–603 respectively) of conductive line 111 (having a width of 0.25 $\mu$m).

In an example, the constant is 0.723 for line 601 in FIG. 6, assuming the conductive material is aluminum, dielectric layer underlying line 601 has a thickness of 1.0 μm, the wavelength of probe beam is 1.48 μm, and reflectance is 0.9. Therefore, probe beam's incident power is 1.1 mW, reflected power is 1.0 mW (in the absence of heating beam) thereby resulting in reflectance R of 0.9 that is used in the above formula to compute the constant 0.723. Thereafter, apparatus 13 divides a slope ($\Delta R/\Delta P$) computed as described above in reference to FIG. 6 with the constant to determine the resistance per unit length. Therefore, in the above-described example, apparatus 13 divides the value 0.5 of ($\Delta R/\Delta P$) with the constant 0.723 to obtain a value 0.361 for the resistance per unit length (in units of ohms/cm). If necessary, resistivity $\rho_e$ is found from the resistance per unit length $\rho_e/Wh_m$ using known values of line width W and line thickness $h_m$. The just-described resistivity $\rho_e$ is at the Debye temperature, and can be used in equation (19) to obtain resistivity at any other temperature.

In equation (20) there is an extra factor of $\sqrt{h_m}$ in the numerator, but the thickness $h_m$ is known (at least approximately), and variations in thickness have a relatively small effect (e.g. less than 1% because thickness is typically known to better than 2%), especially considering that equation (2) requires the square root of $h_m$. As the resistance per unit length is $\rho_e/Wh_m$, changes in the measured voltage level correspond to changes in the resistance per unit length.

The resistivity and slope with respect to temperature for a few metals are:

| Metal | Resistivity @ 20 C ($\Omega$ – cm) | $\frac{\partial \rho_e}{\partial T}$ ($\Omega$ – cm/deg K) |
|---|---|---|
| Aluminum | $2.23 \times 10^{-6}$ | $1.2 \times 10^{-8}$ |
| Copper | $1.72 \times 10^{-6}$ | $7.0 \times 10^{-9}$ |
| Gold | $2.44 \times 10^{-6}$ | $9.1 \times 10^{-9}$ |
| Nickel | $7.80 \times 10^{-6}$ | $3.4 \times 10^{-8}$ |

For an aluminum line with 0.25 μm width and 0.5 μm thickness, reflectance of 0.9, heating power of 5 mW at 830 nm, and probe power of 1 mW at 1.48 μm, the reflected power is 2.7 microwatt.

Figure 4B:
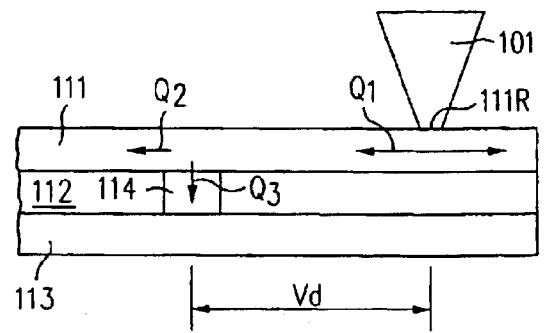
FIG. 4B illustrates, in a cross-sectional view, a via 114 that couples conductive line 111 of the type illustrated in FIG. 4A to another conductive line 113, and the transfer of heat from line 111 by conduction through the via.

As illustrated in FIG. 4B, when heated region 111R is adjacent to a via 114 that connects line 111 to another conductive line 113 underneath dielectric layer 112, the heat generated by beam 101 branches into two components, of which one component flows through via 114. Specifically, heat Q1 generated by beam 101 in line 111 in the negative X direction branches into (1) a first component heat Q2 in line 111 beyond the location of via 114, and (2) a second component heat Q3 that flows through via 114. As Q1=Q2+Q3, any change in the magnitude of Q3 (e.g. due to a defect in via 114 caused by partially filled metal), affects the magnitude of heat Q1 diffusing out of heated region Therefore, a measurement of the reflected power in region 111R at a distance $V_d$ from defective via 114 is higher than a corresponding reflectance measurement at the same distance $V_d$ from a normal (non-defective via) Note that distance $V_d$ is smaller than the length L for the reflectance measurement to have a noticeable difference. For example, with reference to the change in temperature shown in FIG. 5, $V_d$ can be chosen to be 5 microns, when length L is about 20 microns. Assuming the heat flow branches approximately equally between via 114 and line 111 (e.g. Q2=Q3), a defective via may result in result in a 50% increase in the reflected power measurement (at distance Vd) when compared to a measurement near a non-defective via.

Therefore, in one implementation, reflected power measurements are performed adjacent to a number of vias, and each reflected power measurement that is noticeably greater (e.g. 25% greater) than the average measurement of a majority of the vias is flagged as indicating a defective via.

Such measurements could also be performed in a general manner in a predetermined set of regions (that are a fraction of the total number of regions) related to vias (as described above), to detect a problem with the process of forming vias that results in defective vias. If no defective vias are found the wafer is processed further in the normal manner (to form additional layers such as a dielectric layer followed by a metallization layer). If a defective via is found, the wafer is identified as defective and placed in a cassette for further analysis (e.g. by probing, by sectioning or by scanning by electron microscope).

The measured signal level and the signal-to-noise ratio (SNR) is calculated as follows. Equation (20) gives the power of the reflected portion of probe beam 102 as a function of the power of heating beam 101. If A (in units of amps/watt) is the conversion efficiency of photodetector 320 (FIG. 3), then the signal is generated as a current:

$$I_{sig} = A\Delta R(P_L)P_p \tag{21}$$

where reflectance $\Delta R$ $(P_L)$ is given in equation (20) and $P_p$ is the power of probe beam 102 ($P_L$ is the power of heating beam 101 used to generate the temperature distribution)

In one embodiment, a signal carried by current $I_{sig}$ is converted to a signal indicated by a voltage level using a transimpedance amplifier 324 (FIG. 3), and then amplified with a second amplifier 323, which is an amplifier providing a fixed voltage gain adjustable over the range of 10× to 1000×. If the transimpedance gain is $T_g$ (in units of volts/amp) and the amplifier gain is G, then the final signal has the voltage level:

$$V_{sig} = GT_g I_{sig} = GT_g A\Delta R(P_L)P_p \tag{22}$$

Noise in the measured signal can arise from two components—noise in beam 101 and shot noise in photodetector 320. Typically, shot noise exceeds the noise in beam 101. The (RMS) of current due to shot: noise is $$I_{noise} = A\sqrt{2q\left(\frac{P_p}{A}\right)(BW)} = \sqrt{2qAP_p(BW)} \tag{23}$$

where BW is the noise bandwidth and q is the electron charge. For a probe beam 102 having power $P_p=1$ milliwatt, a noise bandwidth of 0.2 Hz, and a conversion efficiency of 0.5 Amp/watt, the noise power is 11.3 picowatts and the noise current is 5.7 picoamps.

An equation for the signal-to-noise ratio is $$SNR = \Delta R(P_L)\sqrt{\frac{AP_p}{2q(BW)}} \tag{24}$$

For the values of reflected power given above (2.7$\mu$ watt for aluminum), the SNR is $6.8\times10^4$.

The predetermined frequency f at which heating beam 101 is modulated can be made as low as necessary to provide a low noise bandwidth required in a particular case. However, as frequency f is reduced, lock-in amplifier 322 (FIG. 3) must observe an increasing number of cycles of the modulation, thereby increasing the measurement time and decreasing the throughput. A predetermined frequency of 100 Hz allows measurement in a period of 0.1 sec that is typically compatible with commercial throughput requirements for processing production wafers, e.g. 2 minutes per wafer may be provided for the inspection of 13 sites on wafer 105 (FIG. 1A). Under these conditions, the measurement period of 0.1 sec per site is negligible, and most of the throughput time may be used to load and position wafer 105 in measurement apparatus 13.

In one implementation, two coaxial laser beams with wavelengths of 830 and 1480 nanometers (for heating and probe beams respectively) are focused onto a series of glass slides (not shown). Each of the glass slides have an aluminum coating of a different thickness in the range of 400 to 1600 angstroms and was 1 inch wide and 3 inches long. A 0.9 NA objective lens provides the 830 nm laser in a spot of diameter approximately 1 $\mu$m. The beam from the 830 nm laser is modulated at 1 KHz. The reflected portion of 1480 nm wavelength beam is sent through a narrow band filter to a germanium detector. The signal is then fed to a lock-in amplifier and detected synchronously with the 830 nm laser modulation.

Figure 7:
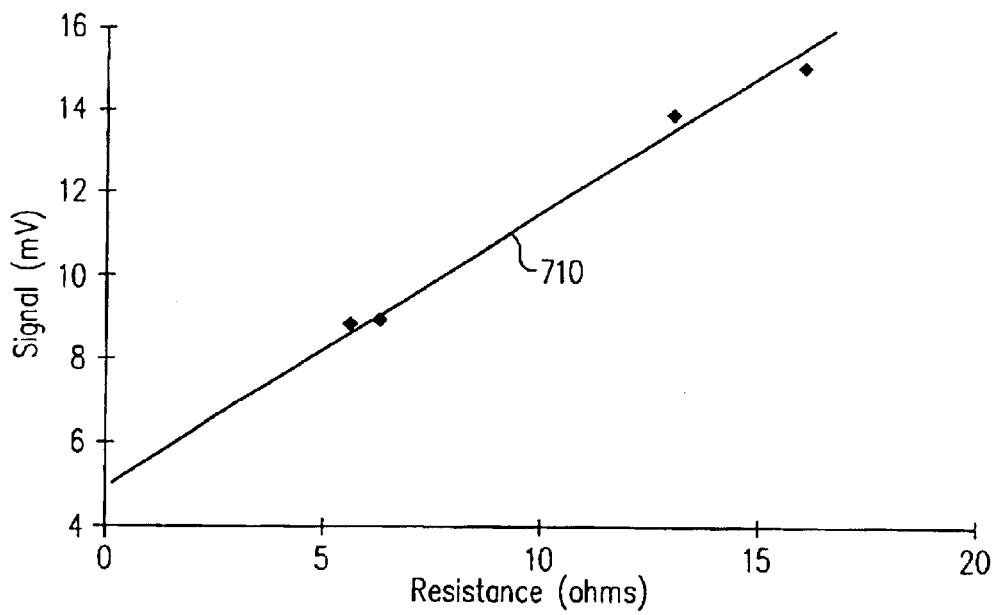
FIG. 7 illustrates, in a graph, a signal generated by the amplifier of FIG. 3 for multiple lines 111 having different resistances, when all lines 111 have the same reflectance (i.e. are formed of the same material).

The resistance between the two ends of each of the just-described glass slides is also measured (with an ohm meter). FIG. 7 illustrates, in a graph, a scatter plot comparing the measured resistance (X-axis) with the measured reflection signal (Y-axis). A straight line 710 (also called "correlation line") correlates the points on the graph, and illustrates the relationship between the actual resistance and the measured reflectance. The linear correlation shown by line 710 indicates the theoretical basis for use of method 200 (FIG. 2) to obtain a resistance measure, as described above.

Numerous modifications and adaptations of the above-described embodiments will become apparent to a person skilled in the art of using lasers to measure semiconductor properties. For example, in an alternative embodiment, instead of using a laser to generate heating beam 101 to change peak temperature Tp, another heat source (such as an electron gun) is used to modulate the temperature T of a conductive line in a wafer. Use of electrons in beam 101 instead of photons allows the diameter of beam 101 to be made smaller than possible when using photons. However, use of electrons in beam 101 requires measurement apparatus 13 to include a vacuum chamber to contain the electron source.

Also, instead of measuring the steady-state ratio in a heated region (e.g. in region 111R), the measurement is performed in a region different from heated region 111R in another embodiment. Although multiple measurements along conductive line 111 have been described above, such measurements need not be performed in a linear manner (e.g. along a straight line. Instead, method 200 (FIG. 2) can be used to perform measurements in an area, by focusing heating beam 101 in three different regions successively (by performing act 202 for a first region, followed by performing act 210 for a second and third region), wherein the three regions together define a triangular area on conductive line 111, and measuring the power of the reflected portion of the probe beam at each of the three regions.

Note that the just-described method need not be performed on a single conductive line 111, and instead each of the three regions could be on three different conductive lines. Moreover, the three different regions can be regions of a planar metallized area (not shown) of wafer 103 as described below in reference to FIGS. 8A, 8B and 9. Also, instead of only three regions, a larger number (e.g. 100 regions) can be used to generate a two dimensional graph (e.g. when the regions form a 10×10 array) of the conductance of such a metallized area.

Furthermore, in another embodiment, a polarized beam of light is focused on region 111R, and a polarization rotation upon reflection is measured by interference, as described in the related U.S. patent application Ser. No. PCT/US99/13084, incorporated by reference above.

In another embodiment, the method is used to measure the properties of the underlying dielectric layer 112 (FIG. 1B).

Specifically, the thermal profile (that indicates temperature as a function of distance of a point in layer 112 from line 111) is governed both by the characteristics (e.g. the thickness, width and thermal or electrical conductivity) of line 111, and by the characteristics (e.g. the thickness and thermal conductivity) of dielectric layer 112.

Therefore, in one embodiment the characteristics (such as resistivity, thickness, and thermal conductivity) of a metal film (that is normally etched to form line 111) are determined using a conventional method, and variations in the thickness or thermal conductivity of the underlying dielectric layer 112 are measured using the relationship in equation (20). In one implementation, characteristics of the metal film are determined by use of a four point probe. In another implementation, two wafers are prepared in an identical manner except for the following differences: a first wafer includes, in dielectric layer 112, a known material, e.g. silicon dioxide, and a second wafer includes, in dielectric layer 112, a material for which the properties are to be determined. The first wafer is used to measure the properties of conductive line 111 (using reflectance measurements as described above), and thereafter the measured properties are used to determine the characteristics of dielectric layer 112.

In another embodiment, measurements are performed on an unpatterned layer of conductive material, such as a layer formed by blanket deposition over all regions of a wafer. In one implementation, the properties of the conductive layer as a whole are substituted for the corresponding variables. Moreover, for a conductive, layer, the change in reflectance is determined from a solution of an area equation that is similar to equation (20), but written in radial coordinates as follows:

$$\frac{\partial^2 \Delta}{\partial r^2} + \frac{1}{r}\frac{\partial \Delta}{\partial r} - \left(\frac{K_i}{K_m}\frac{1}{h_m h_i}\right)\Delta = 0 \quad (25)$$

where $\Delta$ is the difference between the temperature at a radius r and the ambient temperature, and the other variables are as defined earlier. The temperature profile is given by $$\Delta = \frac{(1-R)P_L}{\pi w_0 K_m}\sqrt{\frac{K_m t_i}{K_i t_m}}\frac{K_0\left(\frac{r}{t_m}\sqrt{\frac{K_i t_m}{K_m t_i}}\right)}{K_1\left(\frac{w_0}{t_m}\sqrt{\frac{K_i t_m}{K_m t_i}}\right)} \quad (26)$$

where $K_0$ and $K_1$ are modified Bessel functions, and the other variables are as defined earlier. Note that the temperature profile for a line, equation (15) was a function of both the line thickness $h_m$ and line width W. In equation (26), the temperature profile for a conductive layer however, is only a function of the thickness $h_m$ of the conductive layer. Therefore, a material property, specifically the resistance per unit thickness $\rho_e/h_m$ (called the sheet resistance, or sheet rho) of the layer is determined as described above in reference to equations (1), (2), and (19).

Figure 8A:
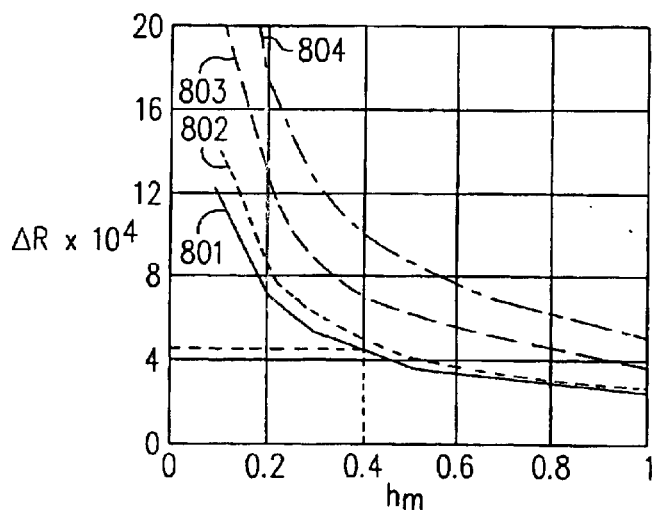
FIG. 8A illustrates, in a graph, the change in reflectance (plotted along y axis and multiplied by 10,000) as a function of the thickness of an aluminum blanket film, with each of lines 801–804 being for a different level of degradation in resistivity.
Figure 8B:
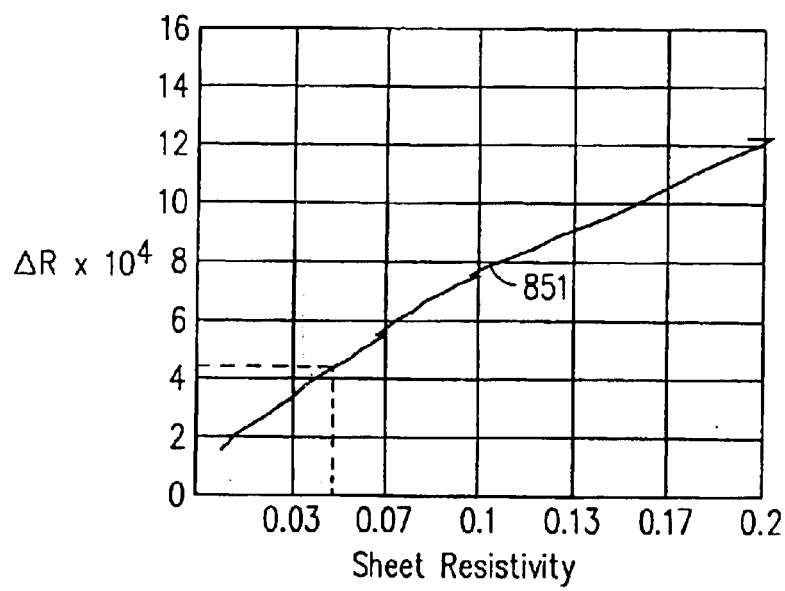
FIG. 8B illustrates, in a graph, the change in reflectance (plotted along y axis and multiplied by 10,000) as a function of the sheet resistivity (in ohms per square) of an aluminum blanket film for no degradation in resistivity.

A numerical model is used to obtain a curved line that relates the change in reflectance (between the presence and absence of a heating beam) to the conductive layer's thickness (see line 801 in FIG. 8A) or between the change in reflectance and the sheet resistance (see line 851 in FIG. 8B). This numerical model is analogous to the model for a conductive line, and uses the relations of equations (1), (2) and (19). FIG. 8A plots on the y axis the change in value of reflectance measurement multiplied by 10,000 and on the x axis the conductive layer's thickness. A laser of 10 milliwatts at 1.48 μm wavelength is used to generate heating beam 101 (FIG. 1B). The four curves illustrated in FIG. 8A are for degradation in the resistivity for an aluminum film of 0 (curve 801), 10% (curve 802), 50% (curve 803), and 100% (curve 804). Therefore, in one example, resistance measurement apparatus 13 measures reflected power from a conductive layer in the presence and absence of heating beam 101, and determines the difference $\Delta R$ to be $4.2\times10^{-4}$. Next, apparatus 13 interpolates, from line 801 (for no degradation) the thickness $h_m$ to be 0.4 μm. Therefore, if the thickness value of 0.4 μm falls within the specification (e.g. a range of 0.38 to 0.42 μm), then the substrate is processed further in the normal manner, and otherwise the substrate is moved out of unit 10 (FIG. 1A) for future analysis. Instead of line 801, any of other lines 802–804 can be used depending on the resistance degradation required by a process. If the thickness $h_m$ is known from another method, the resistance degradation can be determined.

FIG. 8B illustrates, in a graph, the sheet resistance, given by the resistivity divided by the thickness, on the x axis and the change in reflectance multiplied by 10,000 on the y axis. Line 851 is for an aluminum film with resistivity degraded by 0% (in units of ohms/square). Therefore, in the above-described example, resistance measurement apparatus 13 uses the $\Delta R$ value of $4.2\times10^{-4}$ to interpolate, from line 851, the sheet resistivity to be 0.045. Apparatus 13 checks the measured sheet resistivity with the specification for the resistivity in the same manner as that described above in reference to FIG. 8A by comparison with a predetermined range of, e.g. 0.04 to 0.05.

Note that apparatus 13 need not compute a steady state ratio, and instead can use a single reflectance measurement, or a difference between two reflectance measurements to determine the acceptability of a conductive layer (or a conductive line).

Figure 9:
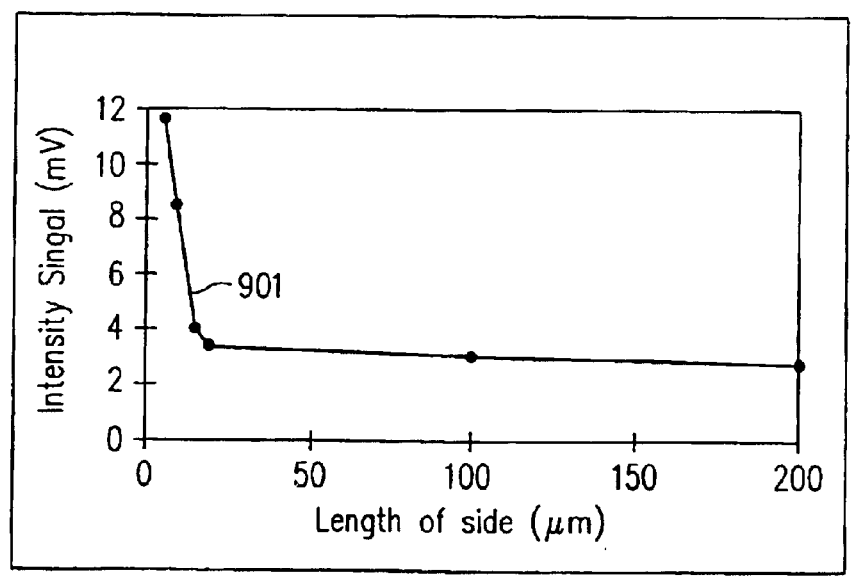
FIG. 9 illustrates, in a graph, an intensity measurement (plotted along y axis in units of millivolts) as a function of length of a side of a square region, for measurements taken at the centers of squares of an aluminum layer 0.2 $\mu$m thick formed on 1 $\mu$m thick silicon dioxide layer that in turn is deposited on a silicon substrate.

A transition from a measurement that is dependent on dimensions parallel to the plane of surface 105 (e.g. for a conductive line) to a measurement that is dependent only on the thickness $h_m$ of the conductive layer (e.g. when the conductive layer is yet to be patterned) occurs when the dimensions in the plane of surface 105 exceed the distance at which the temperature rise becomes negligible. FIG. 9 illustrates, in a graph, measurements taken at the center of square regions, each region having a side of a different dimension from another region. Each region is formed of aluminum and has a thickness of 0.2 μm. The regions have an underlying silicon dioxide insulator that is 1.0 μm thick. The y axis shows the value of reflectance measurement in millivolts and the x axis shows the length of a side of a region. For regions having a small length (e.g. less than 20 μm) the measured value is a function of the dimensions in the plane of the surface. For regions having sides larger than about 20 μm, however, the measured value (also called "signal") is independent of the dimensions in the plane of the surface. Therefore, measurements on regions having sides greater than 20 μm approximate the measurements for the entire layer.

Moreover, in one embodiment, the above-described measurements of the thermal conductivity of dielectric layer 112 are performed in a number of successive regions of the wafer, e.g. in a linear scan across the wafer.

Therefore, numerous such modifications and adaptations of the above-described embodiments are encompassed by the attached claims.

What is claimed is:

1. A method for determining a property of a portion of a substrate, the method comprising:

heating a region of a metal layer in the substrate using power modulated at a frequency that is predetermined to be sufficiently low to ensure that at least a majority of heat is transferred out of the region by diffusion rather than by a thermal wave;

measuring a change in reflectance of the metal layer at the frequency of modulation of the power of heating; and using the change in reflectance in a programmed computer, to determine a measure of electrical conductance of a feature formed by patterning the metal layer.

2. The method of claim 1 wherein:

the frequency is lower than a maximum frequency of 5985 Hz.

3. The method of claim 1 further comprising:

changing the power used in said heating to a new power; and repeating at the new power each of said heating, said measuring and said using in said region.

4. The method of claim 1 further comprising:

repeating said heating, said measuring and said using in another region.

5. The method of claim 1 wherein:

the feature is a via.

6. The method of claim 1 wherein:

the feature is a conductive line.

7. The method of claim 6 wherein:

the measure is resistance per unit length of the conductive line.

8. The method of claim 6 wherein:

said frequency is smaller than a maximum frequency, said maximum frequency being inversely related to at least one of:

length of the conductive line; and a distance at which the temperature of said conductive line is an order of magnitude smaller than the temperature in said region.

9. The method of claim 1 further comprising:

forming the metal layer by using at least one process parameter; and changing the process parameter if necessary depending on the measure of electrical conductance determined during said using.

10. The method of claim 1 wherein:

said measuring comprises using a lock-in amplifier tuned to said frequency.

11. A method for determining a property of a portion of a substrate, the method comprising:

heating a region of conductive material in the substrate using a continuous heat source whose power is modulated at a frequency that is predetermined to be sufficiently low to ensure that at least a majority of heat is transferred out of the region by diffusion rather than by a thermal wave;

measuring a change in reflectance of the region of conductive material at the frequency of modulation of the power of the continuous heat source; and using the change in reflectance of the conductive material in a programmed computer, to determine an indication of thermal conductivity of a dielectric material underneath the conductive material.

12. The method of claim 11 wherein:

the conductive material in the region is unpatterned.

13. The method of claim 11 wherein:

the conductive material in the region is comprised in a plurality of conductive lines.

14. The method of claim 11 further comprising:

changing the power of the continuous heat source used in said heating to a new power; and repeating at the new power each of said heating, said measuring and said using in said region.

15. The method of claim 11 further comprising:

using the thermal conductivity of the dielectric material to determine an indication of a dielectric constant of the dielectric material.

16. The method of claim 11 further comprising:

using the thermal conductivity of the dielectric material to determine an indication of a capacitance between the conductive material and an adjacent conductor.

17. The method of claim 11 further comprising:

using the thermal conductivity of the dielectric material to determine an indication of speed of transmission of signals.

* * * * *